(12) United States Patent
Fourkas et al.

(10) Patent No.: US 9,795,432 B2
(45) Date of Patent: Oct. 24, 2017

(54) CRYOGENIC BALLOON ABLATION INSTRUMENTS AND SYSTEMS

(71) Applicant: Boston Scientific Scimed, Inc., Maple Grove, MN (US)

(72) Inventors: Michael Fourkas, Sunnyvale, CA (US); Steven Walak, Natick, MA (US); Kurt Geitz, Sudbury, MA (US); Kristine Tatsutani, Redwood City, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 281 days.

(21) Appl. No.: 14/196,487

(22) Filed: Mar. 4, 2014

(65) Prior Publication Data
US 2014/0207130 A1  Jul. 24, 2014

Related U.S. Application Data

(60) Continuation of application No. 13/562,150, filed on Jul. 30, 2012, now Pat. No. 8,663,211, which is a
(Continued)

(51) Int. Cl.
*A61B 18/02* (2006.01)
*A61B 17/00* (2006.01)
(Continued)

(52) U.S. Cl.
CPC .............. *A61B 18/02* (2013.01); *A61B 19/54* (2013.01); *A61B 2017/00084* (2013.01);
(Continued)

(58) Field of Classification Search
CPC ................... A61B 18/02; A61B 19/54; A61B 2017/00084; A61B 2017/22051;
(Continued)

(56) References Cited

U.S. PATENT DOCUMENTS 4,619,247 A * 10/1986 Inoue ................. A61B 1/00082
                                                600/116
5,151,100 A *  9/1992 Abele ................. A61B 18/082
                                                606/28
(Continued)

*Primary Examiner* — Daniel Fowler

(57) ABSTRACT

Cryogenic tissue ablation instruments for treating body tissue include an elongate flexible body with a proximal supply port for coupling with a pressurized coolant (e.g., liquid $N_2O$), a supply lumen in fluid communication with the proximal supply port, and an expandable cryogenic balloon carried on a distal portion of the elongate body, the balloon having a wall defining an interior of the balloon. A dispersion member coupled to or otherwise formed out of a distal end portion of the elongate body has an interior lumen in fluid communication with or otherwise comprising a portion of the supply lumen, the dispersion member having one or more coolant dispersion apertures in fluid communication with the balloon interior and sized and located with respect to the balloon wall such that a pressurized flowable coolant in the supply lumen will enter the balloon interior through the one or more apertures in the form of a liquid spray that contacts and provides (through rapid evaporation) substantially uniform cooling of an interior wall surface of a treatment region of the balloon.

21 Claims, 10 Drawing Sheets

Related U.S. Application Data division of application No. 11/763,372, filed on Jun. 14, 2007, now abandoned.

(51) Int. Cl.
 *A61B 17/22* (2006.01)
 *A61B 18/00* (2006.01)
 *A61B 19/00* (2006.01)
 *A61B 90/00* (2016.01)

(52) U.S. Cl.
 CPC ........... *A61B 2017/22051* (2013.01); *A61B 2018/0022* (2013.01); *A61B 2018/0212* (2013.01); *A61B 2019/5437* (2013.01); *A61B 2090/3937* (2016.02)

(58) Field of Classification Search
 CPC .... A61B 2018/0022; A61B 2018/0212; A61B 2019/5437
 USPC ..................................................... 606/20–26
 See application file for complete search history.

(56) References Cited

U.S. PATENT DOCUMENTS

| | | | | |
|---|---|---|---|---|
| 5,281,215 | A * | 1/1994 | Milder | A61B 18/02 606/20 |
| 5,899,898 | A * | 5/1999 | Arless | A61B 18/02 606/20 |
| 6,002,968 | A * | 12/1999 | Edwards | A61B 18/00 606/41 |
| 6,428,534 | B1 * | 8/2002 | Joye | A61B 18/02 606/21 |
| 2005/0165388 | A1 * | 7/2005 | Bhola | A61B 18/1492 606/14 |
| 2005/0251121 | A1 * | 11/2005 | Swanson | A61B 18/02 606/21 |
| 2006/0270981 | A1 * | 11/2006 | Capuano | A61B 18/02 604/113 |
| 2007/0083192 | A1 * | 4/2007 | Welch | A61B 18/1492 606/41 |
| 2007/0299433 | A1 * | 12/2007 | Williams | A61B 18/02 606/21 |

* cited by examiner

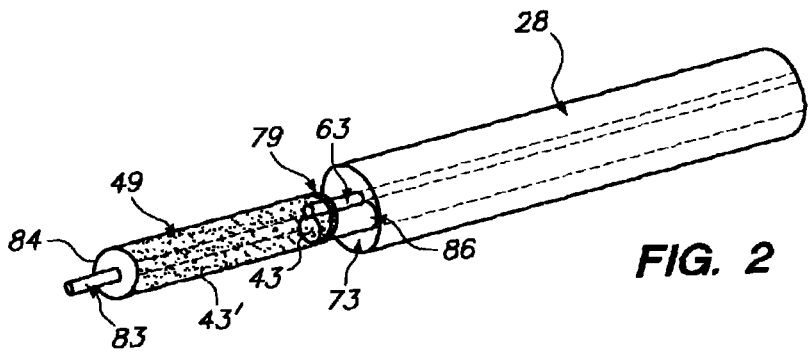
FIG. 2
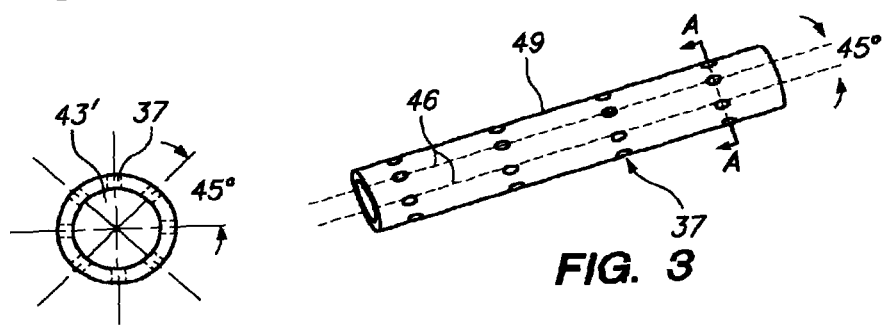
FIG. 3
FIG. 3A
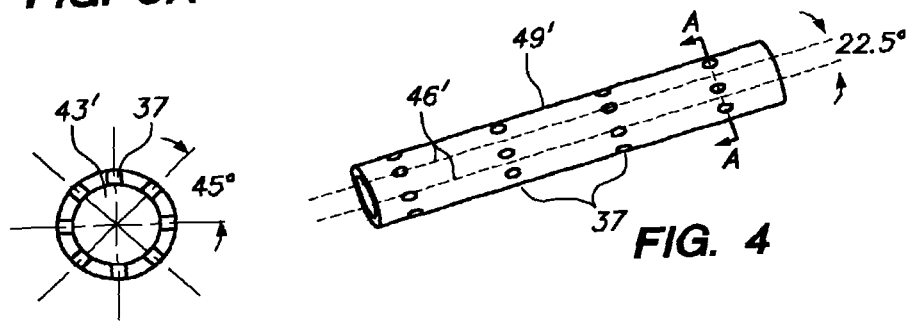
FIG. 4
FIG. 4A
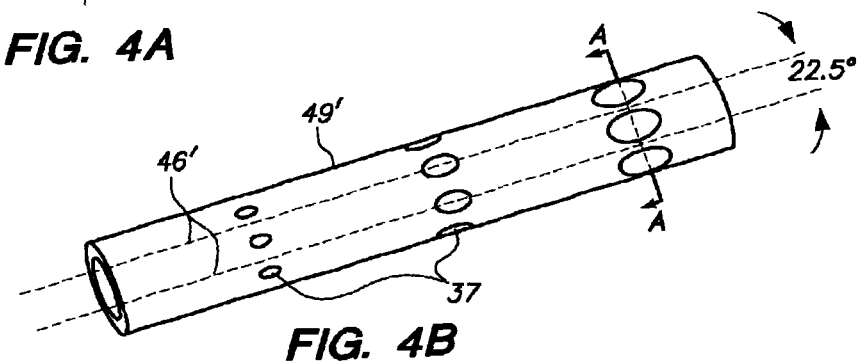
FIG. 4B

SECTION B-B
SCALE 30:1

SECTION A-A
SCALE 30:1

DETAIL C
SCALE 30:1

DETAIL D
SCALE 30:1

CRYOGENIC BALLOON ABLATION INSTRUMENTS AND SYSTEMS

RELATED APPLICATION

This application is a divisional of U.S. patent application Ser. No. 11/763,372, filed on Jun. 14, 2007, which is incorporated by reference as if set forth fully herein.

FIELD OF THE INVENTION

The inventions disclosed herein pertain generally to tissue ablation systems and instruments, and their use for the treatment of body tissues; more particularly, the inventions disclosed herein pertain to cryogenic balloon ablation instruments and their use for treating body tissue, such as esophageal wall tissue for treating Barrett's esophagus.

BACKGROUND

Barnett's esophagus is found in about 10% of patients who seek medical care for heartburn (gastroesophageal reflux or "GERD"), and is considered to be a premalignant condition associated with esophageal cancer. Barrett's esophagus refers to an abnormal change (metaplasia) in the cells of the lower end of the esophagus, which is believed to be caused by damage from chronic stomach acid exposure (reflux esophagitis). Barrett's esophagus is marked by the presence of columnar epithelia in the lower esophagus that replaces the normal squamous cell epithelium. The columnar epithelium is better able to withstand the erosive action of the gastric secretions; however, this metaplasia confers an increased cancer risk of the adenocarcinoma type. The metaplastic columnar cells may be of two types: gastric, which are similar to metaplastic stomach cells (technically not Barrett's esophagus), and intestinal, which are similar to metaplastic cells found in the intestines. A biopsy of the affected area will often contain a mixture of both cell types. Intestinal-type metaplasia confers a higher risk of malignancy, and is usually identified by locating goblet cells in the epithelium.

Both high and low ("cryogenic") temperature tissue ablation treatments are currently offered for treating Barrett's esophagus. As used herein, "tissue ablation" refers to the necrosis, destruction or killing of tissue cells, which may be accomplished using a number of different energy delivery modalities for achieving high or low temperature cell necrosis. By way of one example, U.S. Pat. No. 7,150,745 discloses a system for ablating esophageal tissue by positioning an expandable balloon probe in the area of the esophagus to be treated, the balloon exterior being plated with a large number of surface electrodes that can be selectively activated to convey bi-polar radio frequency electrical energy into the esophageal surface tissue for destroying the Barrett's cells. By way of further examples, U.S. Pat. Nos. 6,027,499, and 7,025,762 disclose cryogenic ablation systems for directly spraying esophageal wall tissue with liquid nitrogen. Cryogenic balloon instruments and systems for (non-ablative) treatment of blood vessel wall tissue are disclosed and described in U.S. Pat. No. 6,468,297 and in U.S. Patent Application Publication No. 20060084962. The foregoing U.S. Pat. Nos. 7,150,745, 6,027,499, 7,025,762 and 7,081,112, and U.S. Patent Application Publication No. 20060084962 are each incorporated herein by reference for all that they teach and disclose.

The objective of these tissue ablation therapies is to destroy the characteristic Barrett's columnar epithelium layer, without causing unwanted damage to underlying submucosa tissue or surrounding healthy tissue. In particular, the columnar epithelium characteristic of Barrett's esophagus has been reported to reach lengths of up to 8 cm, and is approximately 500 microns thick. Disruption of deeper tissues in the muscularis mucosae, located at a depth of approximately 1000 microns or deeper, can lead to stricture formation and severe long term complications. On the other hand, missed or buried "islands" of Barrett's cells can result if the therapy does not uniformly encompass all affected tissue areas. Thus, precise control of both the ablation tissue surface area and "kill depth" are highly desirable.

SUMMARY OF THE DISCLOSED INVENTIONS

In one embodiment of the disclosed inventions, a cryogenic tissue ablation instrument comprises an elongate flexible body having a proximal supply port adapted for coupling with a source of pressurized flowable coolant, e.g., liquid nitrous oxide ($N_2O$), and a coolant supply lumen in fluid communication with the proximal supply port and extending through the elongate body to a distal portion thereof. A tubular dispersion member is coupled to or otherwise formed from the distal end portion of the elongate body, and has an inner lumen that is in fluid communication with (or an extension of) the elongate body supply lumen. An expandable balloon is carried on the distal portion of the elongate body, an interior wall surface of the balloon defining an interior of the balloon. The balloon is preferably at least semi-compliant and transparent, although embodiments employing a non-compliant and/or non-transparent balloon are also contemplated. The dispersion member at least partially extends into the balloon interior and has a plurality of coolant dispersion apertures formed therein in fluid communication with the respective coolant supply lumen and balloon interior. In particular, the coolant dispersion apertures are sized and located on the dispersion member so that a pressurized flowable coolant in the supply lumen will enter the balloon interior through the dispersion apertures in the form of a liquid spray that contacts and provides (through rapid evaporation) substantially uniform cooling of the interior balloon wall surface of a treatment region of the balloon. Gas formed as a result of the coolant evaporation is carried through an exhaust passage or lumen in the elongate body and released through a relief valve at a proximal end thereof.

In various embodiments, the treatment region may include anywhere from only a limited circumferential portion of the balloon wall up to the entire circumference, and may extend a substantial portion (e.g., 3-4 cm in embodiments used for treating esophageal wall tissue) of the axial balloon length. The coolant dispersion apertures may be offset axially, circumferentially, or both, on the dispersion member. In one embodiment, a first plurality of circumferentially spaced apertures is located proximally of a second plurality of circumferentially spaced apertures on the dispersion member. The apertures may be substantially uniform in size, or if needed in order to compensate for pressure losses within the supply lumen, more proximally located apertures may be smaller than more distally located ones, with a uniform spray against the entire (or a sizable portion of the) interior balloon wall being desirable. In various embodiments, the coolant dispersion apertures may have shapes such as circular, rectangular (e.g., slots), or elliptical, although other shapes may be employed. In one embodiment, instead of a plurality of coolant dispersion apertures, one or more diffusers and/or deflectors may be provided along the dispersion member, each configured to direct a liquid spray of coolant from the supply dispersion member lumen onto the interior balloon wall surface.

In embodiments used in treating esophageal wall tissue, the balloon preferably has a collapsed delivery profile sized for passage through a working channel of an endoscopic instrument (e.g., a conventional GI gastroscope) into a human esophagus, and an expanded treatment profile sized slightly greater than the interior of the esophagus such that, when the balloon is transitioned from its collapsed delivery profile to its expanded treatment profile, an exterior surface of the balloon wall makes substantially uniform contact with and smoothes out the surrounding esophageal wall tissue. The balloon is preferably sized and has a compliance such that, as it transitions from its delivery profile to its expanded profile, it contacts and smoothes the esophageal wall tissue. The balloon wall exterior may be made of or coated with, a lubricious material to assist in its positioning within, and smoothing of the esophageal wall tissue.

In some embodiments, the balloon wall comprises a first material, e.g., a polymer, with a second (non-polymer) material having greater thermal conductivity than the first material distributed in the balloon in such quantity and configuration so as to substantially increase the thermal conductivity of the balloon above the conductivity it would have in the absence of the second material. By way of non-limiting examples, the second material may comprise thin metallic strips, fibers, or particles attached to and/or embedded (e.g., impregnated) in the balloon wall.

The balloon wall may be made of an optically clear material to allow for direct visualization through the balloon wall using a viewing device positioned proximally of the balloon when the balloon is delivered and expanded in the patient's body. This allows an attending physician to position the balloon using a viewing apparatus carried, e.g., in a same endoscopic delivery device used to deliver the balloon. Hemispherical balloon ends may be employed to reduce distortion and further facilitate direct visualization through the balloon wall.

In embodiments of the disclosed inventions, a medical treatment system including the cryogenic balloon instrument further includes a source of pressurized flowable coolant, e.g., a canister of liquid $N_2O$, coupled to the proximal supply port of the instrument, and a controller operatively coupled with the coolant source so as to so controllable release the coolant into the supply lumen. The system may optionally include one or more temperature sensors carried on or in the dispersion member and/or balloon wall in the treatment region of the balloon. The temperature sensors are operatively coupled to the controller, wherein the controller may be configured to regulate the release of coolant into the supply lumen based at least in part on temperature measurements obtained from the one or more temperature sensors. Additionally or alternatively, thermochromic material may be carried on and/or in the balloon wall in the treatment region of the balloon, the thermochromatic material selected or calibrated to undergo a visual change in appearance when the balloon wall temperature of the treatment region reaches a selected tissue ablation temperature. In this manner, the balloon temperature can be monitored by an attending physician using a viewing apparatus carried in an endoscopic delivery device.

In some embodiments, the elongate body is provided with a plurality of circumferentially spaced coolant supply lumens, each in fluid communication with the proximal supply port and extending through the elongate body to respective corresponding inner lumens of the dispersion member. In such embodiments, respective pluralities of coolant dispersion apertures are provided in the dispersion member such that each plurality of coolant dispersion apertures is in fluid communication with a respective one of the coolant supply lumens. The collective apertures are sized and located on the dispersion member such that a pressurized flowable coolant in a respective supply (and dispersion member) lumen will enter the balloon interior in the form of a liquid spray that contacts and provides (due to rapid evaporation) substantially uniform cooling of the interior wall surface of a treatment region of the balloon.

In one such embodiment, each plurality of coolant dispersion apertures includes a first aperture having a first aperture size in communication with a respective coolant supply lumen, and a second aperture located distally on the dispersion member from the first aperture in communication with the same coolant supply lumen, the second aperture having a second aperture size the same or greater than the fast aperture size. In another such embodiment, the respective dispersion apertures are provided in sets of circumferentially spaced apertures along the dispersion member within the balloon interior, each set including respective apertures in fluid communication with a corresponding one of the respective coolant supply lumens. In yet another such embodiment, the portion of the dispersion member extending into the balloon interior is itself an expandable body, with the respective coolant dispersion apertures located on an exterior surface of this inner expandable body.

In one embodiment, the treatment region is a distal facing portion of the balloon wall, the coolant dispersion aperture (s) being located relative to the balloon such that a pressurized flowable coolant in the supply lumen is directed axially in the form of a liquid spray applied against the interior surface of the distal balloon wall portion. In another embodiment, the energy delivery portion is a side (i.e., lateral relative to the longitudinal axis of the balloon) facing portion of the balloon wall, the dispersion aperture(s) being located relative to the balloon such that a pressurized flowable coolant in the supply lumen is directed radially in the form of a liquid spray applied against the interior surface of the respective balloon side wall portion.

In one embodiment, the balloon is a multi-lobe balloon having a plurality of isolated, separately inflatable balloon chambers, wherein each balloon chamber may be selectively placed in fluid communication with a respective coolant supply lumen extending through the elongate body. Alternatively or additionally, the respective balloon chambers may also be selectively placed in fluid communication with independent fluid or gas inflation sources (other than the coolant) through further respective lumens extending through the elongate body. The dispersion member extends through a central region of the multi-lobe balloon, wherein the coolant supply lumens are selectively placed in fluid communication with a respective one of the interior balloon chambers via a respective plurality of coolant dispersion apertures formed in the dispersion member. The respective dispersion apertures are sized and located on the dispersion member such that a pressurized flowable coolant in any of the supply lumens will enter the respective balloon chamber in the form of a liquid spray that contacts and provides cooling of an interior wall surface of the respective chamber. In a treatment system including a multi-lobe balloon embodiment further includes a source of pressurized flowable coolant fluidly coupled to the respective instrument supply ports, and a controller operatively coupled with the source of pressurized flowable coolant. The controller is configured to selectively, independently and controllably release the coolant into one or more of the supply lumens. Gas formed as a result of coolant evaporation in any of the respective balloon lobes may be carried through a common (or separate) exhaust lumen in the elongate body and released though a respective relief valve located at a proximal end thereof.

In still another embodiment, a method is provided for ablating wall tissue using a cryogenic balloon instrument, the instrument comprising an elongate flexible member carrying an expandable balloon on a distal end thereof the balloon having a collapsed delivery shape and an inflated treatment shape, the method including positioning the cryogenic balloon while in its collapsed delivery shape through a working channel of an endoscopic instrument to a desired location in a patient's body (e.g., esophagus) to be treated; inflating the cryogenic balloon so that an outer wall surface thereof makes substantially uniform contact with, and smoothes the wall tissue to be treated; and delivering a pressurized flowable coolant from a source external to the patient through a supply lumen in the elongate body and out one or more dispersion apertures in fluid communication with the supply lumen, the one or more dispersion apertures sized and located such that the pressurized flowable coolant enters the balloon interior in the form of a liquid spray that contacts and provides (through rapid evaporation) substantially uniform cooling of the interior balloon wall surface of a treatment region of the balloon. Gas formed as a result of evaporation of the coolant within the balloon interior may be purged through an exhaust lumen extending from the balloon interior to a relief valve located at a proximal end of the elongate body.

Other and further embodiments, aspects and features of the disclosed embodiments will become apparent to those skilled in the art in view of the accompanying figures and the following detailed description.

BRIEF DESCRIPTION OF THE DRAWINGS

The drawings illustrate the design and utility of embodiments of the disclosed inventions, in which similar elements are referred to by common reference numerals, and in which:

FIG. 2 is a simplified, partially cut-away perspective view of a tubular dispersion member connected to a distal end portion of a cryogenic balloon instrument used in the system of FIG. 1A.

FIGS. 3 and 3A depict one embodiment of a tubular dispersion member that extends axially through the cryogenic balloon in FIG. 1B, including a first configuration of coolant dispersion apertures for introducing a pressurized coolant into the balloon interior.

FIGS. 4 and 4A depict another embodiment of the tubular dispersion member that extends axially through the cryogenic balloon in FIG. 1B, including an alternate configuration of coolant dispersion apertures for introducing a pressurized coolant into the balloon interior.

FIG. 4B depicts another embodiment of the tubular dispersion member that extends axially through the cryogenic balloon in FIG. 1B, including yet another alternate configuration of coolant dispersion apertures for introducing a pressurized coolant into the balloon interior.

DETAILED DESCRIPTION

Figure 1A:
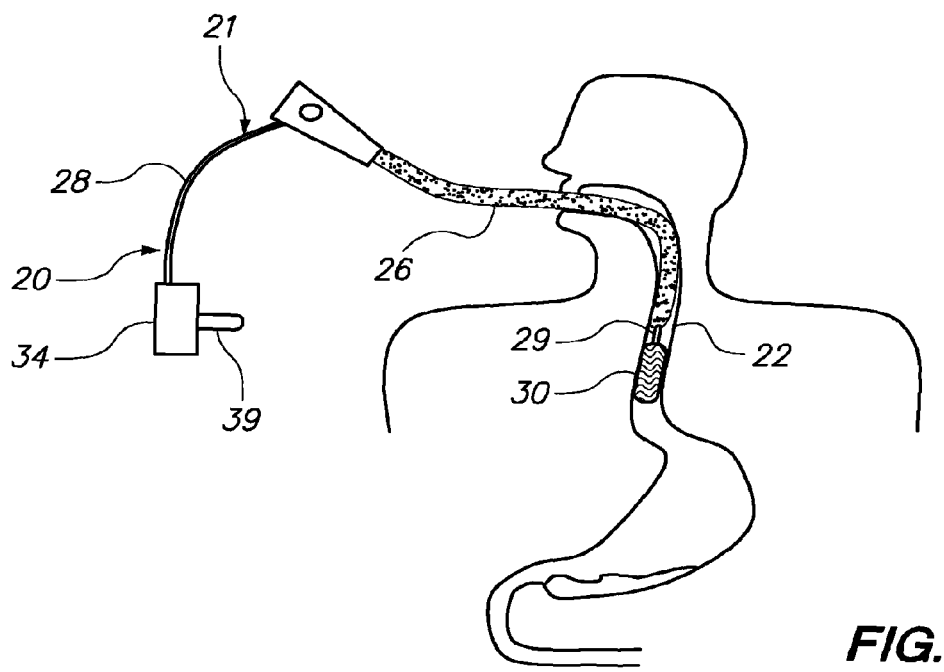
FIG. 1A is a simplified schematic illustration of a system used for treating esophageal tissue using a cryogenic balloon instrument constructed and positioned in the esophagus according to one embodiment.

Embodiments of the inventions disclosed and described herein are directed to cryogenic balloon systems and their use for treating body tissue, in particular but not limited to esophageal wall tissue. By way of non-limiting examples, embodiments of the invention include elongate flexible instrument carrying cryogenic balloons designed for introduction through a working channel of a standard GI gastroscope into a patient's esophagus, and then expanded to contact and smooth the esophagus wall, thereafter producing a controlled and substantially uniform "cold zone" that will kill characteristic Barrett's esophagus columnar epithelium cells in the esophageal wall tissue, without unduly harming tissues in the muscularis mucosae or deeper. The following detailed description is directed to such embodiments used for treating esophageal tissue. However, such embodiments are disclosed and described by way of illustration, and not limitation, and other and different balloon embodiments configured for treating body tissue regions other than the esophagus are also contemplated herein.

For purposes of illustration, and with reference generally to exemplary embodiments of the disclosed inventions, ablative cooling for destroying the columnar epithelium cells is achieved by evaporation of a flowable coolant, e.g., liquid nitrous oxide ($N_2O$), sprayed in a substantially uniform manner onto an interior wall surface of a dilation-type balloon positioned in the esophagus being treated. The balloon may be compliant, semi-compliant, non-compliant, depending on the particular embodiment, but is preferably at least semi-compliant in embodiments used for treating esophageal wall tissue. The coolant is released from a high pressure cylinder into one or more confined supply lumens of a relatively small diameter elongate flexible instrument, and driven down a pressure gradient to a distal portion of the instrument on which the cryogenic balloon is carried.

Within the balloon, the coolant is allowed to escape through one or more, relatively small coolant dispersion apertures in a dispersion member coupled to or otherwise formed from a distal end portion of the elongate instrument body, the dispersion apertures in fluid communication with the respective supply lumen(s) and balloon interior. The supply line pressure and aperture sizing are configured such that the coolant sprays against an inside surface of the balloon wall and evaporates rapidly, thereby creating a corresponding rapid cooling of the balloon wall and surrounding environment within the balloon interior.

The balloon may be initially inflated by releasing a controlled pulse of coolant, and the supply line pressure is thereafter maintained at a level close to the source pressure, e.g., approximately 800 psi or higher, in order to maintain the coolant in liquid form. It will be appreciated that the system pressure will undergo a significant drop across the coolant apertures (i.e., between the supply lumen(s) and the balloon interior), with a balloon and exhaust lumen pressure preferably maintained at less than 100 psi, and preferably in a range of 5-50 psi. The coolant dispersion aperture(s) are preferably sized so as to preferably create a continuous spray (or mist) of coolant there through. The coolant dispersion aperture(s) are located on the dispersion member so that a substantially uniform temperature distribution along a treatment region of the balloon surface is achieved. The treatment region may include only a portion or the entire circumference of the balloon. Gas formed as a result of coolant evaporation is carried through an exhaust lumen in fluid communication with the balloon interior and extending through the elongate body, wherein the gas is released through a relief valve located at a proximal end of the instrument, the relief valve pressure setting selected to maintain a desired balloon inflation pressure, taking into account losses incurred through the exhaust lumen.

Figure 18:
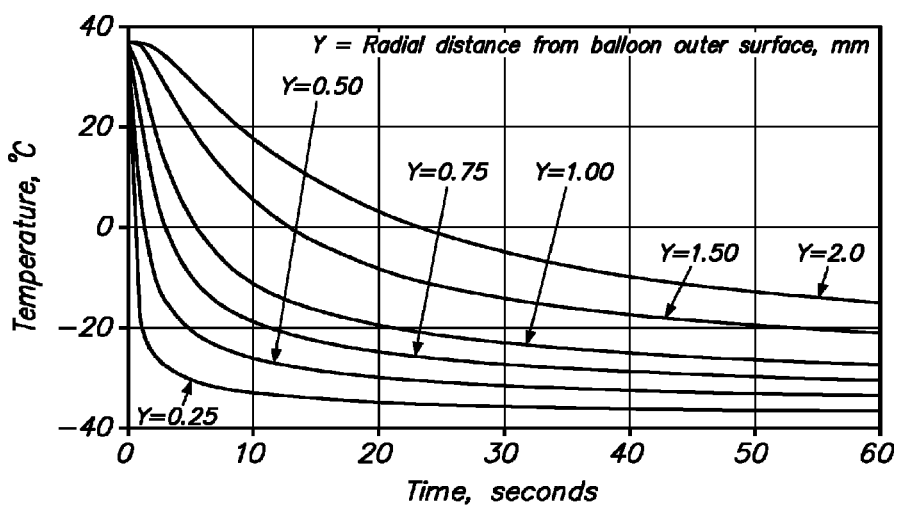
FIG. 18 is an illustrative plot of computer simulation of tissue temperature-versus-time at varying tissue depths of a human esophagus when contacted by a balloon wall having a temperature of −40° C.

The volume of liquid coolant and the evaporation pressure are controlled to produce an exterior balloon treatment surface temperature reaching as low as $-80°$ C. to $-90°$ C., although more preferably the balloon wall will be cooled within an operating range of $-30°$ C. to $-40°$ C. for a time period of 10-20 seconds, which is believe sufficient for achieving a uniform tissue kill depth, e.g., 500 microns, sufficient to destroy Barrett's cells when treating the esophagus, without causing harm to the deeper submucosal tissue. Computer simulations were performed to calculate the subsurface temperature profile in esophageal tissue placed in thermal contact with man 18 mm diameter cryogenic balloon catheter with respective balloon wall temperatures of $-20°$ C., $-40°$ C., $-60°$ C. and $-80°$ C. A plot of tissue-temperature-versus-time at varying tissue depths based on such computer simulations is shown in FIG. 18. These simulations show that temperatures between approximately $-30°$ C. and $-20°$ C. are expected at tissue depths between 500 and 1000 microns from the surface after 30 seconds surface contact time using a balloon having a $-40°$ C. wall temperature. It will be appreciated by those skilled in the art that the actual balloon surface temperature and time parameters may be varied, depending on patient parameters and the tissue being treated, among other factors.

In an exemplary embodiment, the cryogenic balloon has a delivery configuration designed to pass through the working channel of an upper GI gastroscope and an expanded profile sized to make solid uniform contact with, and smooth the esophageal wall tissue to be treated. In various embodiments, the folded balloon configuration has a profile (or diameter) less than 3.7 mm, preferably less than 2.8 mm, and more preferably less than or equal to 2.5 mm. In particular, a range of balloons varying from 18 mm to 34 mm in diameter may be employed to cover the full size range of the human esophagus, with appropriate sizing to assure good contact between the balloon and esophageal wall tissue. The length of the active treatment region of the balloon may vary, but is preferably between 3 and 4 cm for treatment of human esophageal wall tissue. The treatment region may include the entire circumference of the balloon, or may be focused to a more limited energy delivery balloon wall surface. In various embodiments, the total working length of the elongate instrument will be greater than 120 cm and preferably equal to or greater than 180 cm to allow for passage through standard endoscopes. It will be appreciated that the balloon may be provided in different (expanded treatment) dimensions, depending in part on compliancy, in order to treat a full range of human esophagus sizes.

To initiate treatment, the distal portion of the elongate instrument and balloon are advanced through the working channel of the gastroscope, until the balloon is extended beyond the open tip and positioned in a targeted area of the patient's esophagus. The balloon is then expanded using an initial pulse of coolant released from the source through the supply lumen(s) into the balloon. This initial inflation pulse is preferably sufficient to inflate the balloon to its full inflation pressure to contact and smooth the esophagus wall, without also causing significant cooling of the balloon wall. Once the balloon is inflated and its position relative to the tissue being treated is confirmed, substantial and rapid cooling of the balloon wall is initiated by the controlled release and evaporation of a liquid coolant against the inner wall of the balloon, until the surface temperature in the treatment region of the balloon is reaches a desired tissue ablation temperature. The balloon is then maintained at this temperature (or within a close range thereto) for a specified treatment period, e.g., in a temperature range of −30° C. to −40° C. for a time period of 10-20 seconds, for killing all cells in the contacting esophageal tissue up to a depth of about 500 microns, without harming or disrupting cells deeper than about 1000 microns.

Figure 1B:
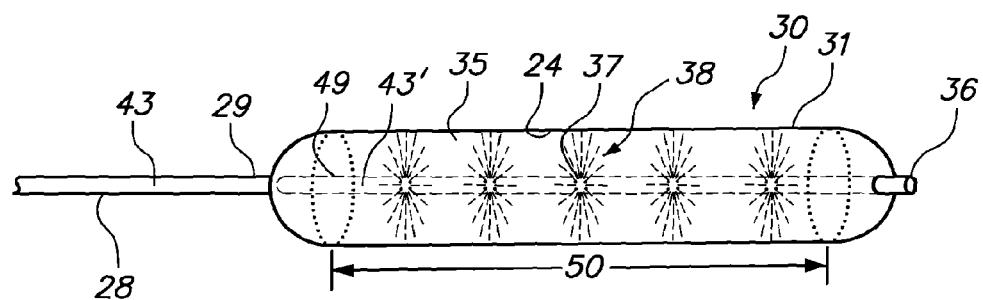
FIG. 1B is a simplified, partially cut-away perspective view of a first embodiment of a cryogenic balloon carried on an elongate instrument body for use in the system of FIG. 1A.
Figure 1C:
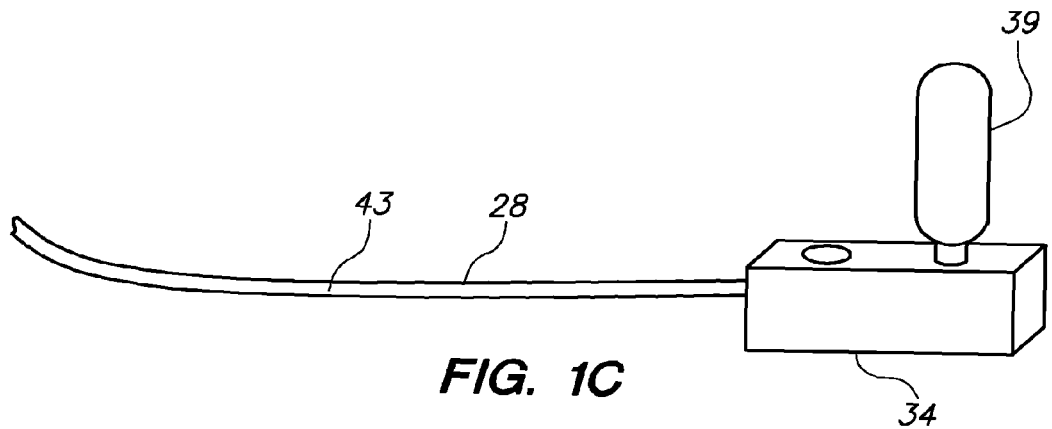
FIG. 1C is a simplified schematic illustration of a controller for use in the system of FIG. 1A.

FIGS. 1A-C depict an exemplary embodiment of a cryogenic balloon system 20 used for treating a patient's esophagus 22. The system 20 generally includes a cryogenic tissue ablation instrument 21 comprising an elongate flexible body 28 having a proximal supply port (not shown) adapted for coupling with a source of pressurized flowable coolant 39 (e.g., a canister of liquid $N_2O$). The elongate body 28 includes an internal supply lumen 43 in fluid communication with the proximal supply port and extending through the elongate body 28 to a distal portion (29) thereof. An expandable balloon 30 is carried on the distal portion 29 of the elongate body 28, the balloon 30 having a wall 31, with an interior surface 24 of the wall defining an interior 35 of the balloon 30. The balloon 30 and instrument distal portion 29 are preferably sized for introduction through a working channel of gastroscope 26 into the patient's esophagus 22.

The balloon 30 may be constructed of a compliant or semi-compliant material in order to improve contact with the wall tissue of the esophagus 22, and minimize a number of discrete balloon sizes needed to treat a full range of human esophagi. The balloon wall 31 is preferably constructed of adequately transparent material that will allow for direct visualization through the balloon wall 31 using a viewing device positioned proximally of the balloon (e.g., a viewing lens of the gastroscope) when the balloon is delivered and expanded in the patient's esophagus 22. This allows an attending physician to position the balloon 30 in the esophagus 22 using a viewing apparatus carried in the endoscopic delivery device. Hemispherical balloon ends may reduce distortion and further facilitate direct visualization through the balloon wall.

A tubular dispersion member 49 is coupled to or otherwise formed from the distal portion 29 of the elongate body 28, and extends through the balloon interior 35 to a distal balloon end anchor 36. The dispersion member 49 has an interior lumen 43' in fluid communication with or otherwise comprising a distal portion of the supply lumen 43, with a plurality of coolant dispersion apertures 37 formed (e.g., laser drilled) in the dispersion member in fluid communication with the respective supply lumen 43 and balloon interior 35. The coolant dispersion apertures 37 are sized and located along the dispersion member 49 such that pressurized coolant in the supply lumen 43 will enter the balloon interior 35 through the respective apertures 37 in the form of a liquid spray 38 that contacts and provides (due to rapid evaporation of the liquid coolant) substantially uniform cooling of an active treatment length or region 50 of the interior balloon wall surface 24. The distal end of the dispersion tube 49 is preferably sealed to force coolant flow through the respective coolant apertures 37.

The system includes a controller 34 operatively coupled with the source of pressurized coolant so as to controllable release the coolant into the supply lumen 43. The controller 34 may be the same or substantially similar to that used for the PolarCath™ vascular cryogenic balloon system distributed by Boston Scientific Corporation, Natick Mass. (www.bsci.com), which is disclosed and described in the above-incorporated U.S. Patent Application Publication No. 20060084962. In particular, the controller 34 is programmed to controllably release the liquid coolant into the respective supply lumen 43 and balloon interior 35 to maintain the balloon wall temperature at a desired operating temperature for a specified time period.

Figure 12:
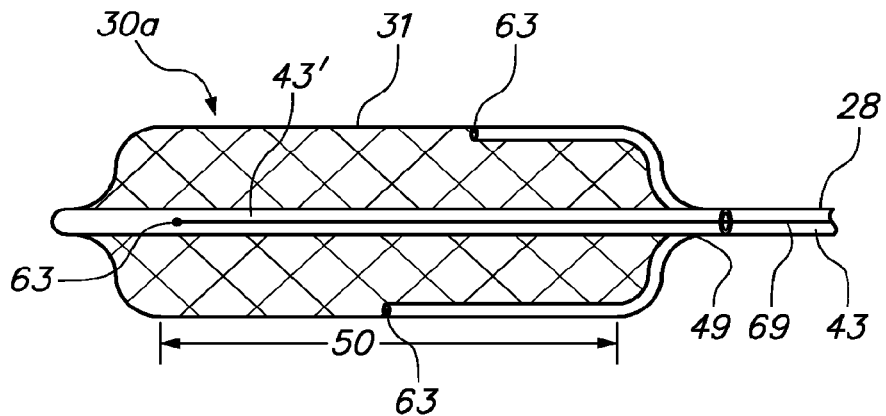
FIG. 12 is a simplified, partially cut-away perspective view of yet another cryogenic balloon embodiment for use in the system of FIG. 1A, in which a plurality of temperature sensors are carried on or in the balloon wall.

Referring briefly to FIG. 12, the system 20 may optionally include one or more temperature sensors 63 carried in the dispersion tube lumen 43' and/or in the balloon wall 31 in the treatment region 50 of the balloon (referred to as 30A), which are operatively coupled to the controller 34 via wires 69 that extend through the elongate body 28. In this configuration, the controller 34 may regulate release of the coolant into the supply lumen 43 based at least in part on input from the one or more temperature sensors 63. In some such embodiments, the measured temperature is monitored as a safety override, wherein the flow of coolant is stopped if the temperature drops below (or rises above) a predetermined threshold. In other embodiments, the measured temperature may be used for controlling the rate of release of the coolant for more precisely regulating the temperature a desired operating point.

Figure 13:
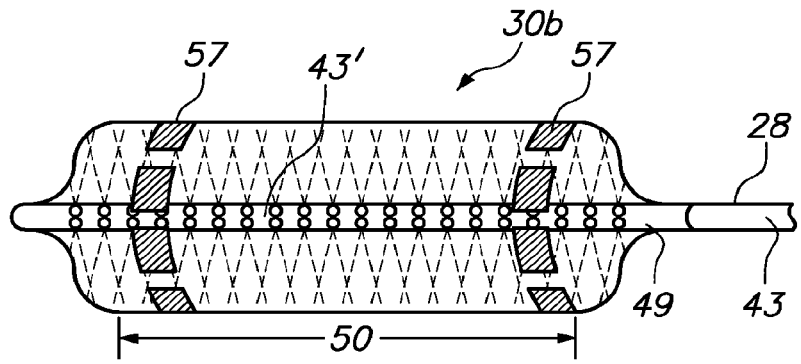
FIG. 13 is a simplified, partially cut-away perspective view of still another cryogenic balloon embodiment for use in the system of FIG. 1A, in which thermochromic material is carried on and/or in the balloon wall.

Referring briefly to FIG. 13, in an alternative embodiment, thermochromic material 57 may be carried on and/or in the balloon wall 31 in the treatment region of the balloon (referred to as 30B), the thermochromatic material 57 selected to undergo a visual change in appearance when the temperature of the balloon wall 31 passes a selected threshold temperature (e.g., −40° C.). In this manner, the temperature of the active balloon region 50 may be monitored visually by an attending physician using a viewing apparatus carried in the gastroscope 26. Notably, in the illustrated balloon 30B, the thermochromatic material 57 is placed at the respective edges of the treatment region 50, although it may be desirable to place the material in other locations, or even to embed the material 57 throughout the balloon wall 31, so that the balloon 30B as a whole changes appearance once the temperature threshold is reached.

Returning to the illustrated balloon 30 of FIG. 1B, the coolant dispersion apertures 37 are sized and located along the dispersion member 49 within the balloon interior 35 such that an entire circumference of the active region 50 undergoes substantially uniform cooling. In turn, the balloon treatment region 50 imparts a substantially uniform temperature gradient on the contacted tissue in the esophagus 22. The temperature of the balloon wall 31 in the active treatment region 50 may be regulated by the controller 34, by regulating the output flow of the coolant, so that the system 20 is able to deliver controlled cryogenic tissue destruction of the Barrett's esophagus columnar epithelium cells in the esophageal wall tissue, without unduly harming deeper tissues, such as the muscularis mucosae or submucosae.

The coolant dispersion apertures 37 can have a number of different shapes, such as circular, rectangular (e.g., a slot), or elliptical. In the case where multiple coolant dispersion apertures 37 are provided, they may be axially offset, circumferentially offset; or both, along the dispersion member 49. In the case of axially offset dispersion apertures, the more proximally located aperture(s) may optionally be made smaller than the more distally located apertures(s) in order to compensate for pressure losses within the coolant supply lumen 43. However, it is believed that a substantially uniform outflow spray against the interior balloon wall 24 can be achieved with substantially uniform sized apertures when they are relatively small, e.g., on the order of 0.001 to 0.008 inches in diameter, and approximately 0.002 inches in diameter in one embodiment.

By way of example, in the illustrated balloon embodiment 30 in FIG. 1B, the coolant dispersion apertures 37 include five, axially offset groupings, or "sets" of apertures 37, each set including a plurality of circumferentially offset apertures. As seen in FIGS. 3 and 3A, in one embodiment, each set of circumferential offset apertures 37 includes eight apertures approximately evenly spaced about the circumference of the dispersion member 49, i.e., with each aperture 37 being offset approximately 45° from adjacent apertures in the same set (best seen in FIG. 3A). Although the respective sets of circumferentially offset apertures 37 are longitudinally (axially) offset (i.e., displaced) along the length of the dispersion member 49, the apertures 37 within an individual set remain aligned in a same relative rotational position about the circumference of the elongate body 28, as illustrated by dashed lines 46.

FIG. 4B depicts a variation of the embodiment shown in FIG. 4A, in which the coolant dispersion apertures of a first circumferentially spaced group of fluid dispersion apertures (designated as 37a) have a first aperture size, a second circumferentially spaced group of fluid dispersion apertures (designated as 37b) spaced distally from the first group along the axis of the fluid dispersion member (designated as 49″) have a second aperture size greater than the first aperture size, and a third circumferentially spaced group of fluid dispersion apertures (designated as 37c) spaced distally from the second group along the axis of the fluid dispersion member have a third aperture size greater than the respective first and second aperture sizes.

With reference to FIGS. 4 and 4A, in an alternative embodiment for use in the cryogenic balloon system 20 of FIG. 1, adjacent sets of coolant dispersion apertures 37 provided on the dispersion member (designated as 49') are both axially and circumferentially offset from one another. In particular, each set of circumferential offset apertures 37 provided in the dispersion member 49' includes eight apertures substantially evenly spaced about the circumference of the dispersion member 49', each aperture 37 of an individual set being offset approximately 45° from adjacent apertures in the same set (best seen in FIG. 4A), with the respective apertures 37 in adjacent sets being collectively offset (rotationally) from one another approximately 22.5° about the circumference, as indicated by the dashed lines 46'.

In one embodiment of the distal end assembly (shown in FIG. 2 without the balloon wall for ease in illustration), the elongate body 28 carries an inner tubular member 86 that defines the supply lumen 43, along with a thermocouple 63 within an interior lumen 73, wherein the remaining annular space in the lumen 73 functions as a gas exhaust lumen. A proximal end of the dispersion member 49 has an interior lumen 43' that receives and surrounds the tubular member 86 and thermocouple 63, with the inner wall of the dispersion member 49 forming a fluid tight bond 79 around the respective tubular member 86 and thermocouple 63, with the supply lumen 43 in fluid communication with an interior lumen 43' of the dispersion member 49. A central stiffening member 83 is provided through the axial center of the dispersion member 49 for structural support (in particular, to resist axial compression). A fluid tight seal 84 is in provided at the distal end of the dispersion member 49, sealing off lumen 43' to force fluid flow through the fluid apertures (not shown in FIG. 2).

Figure 20:
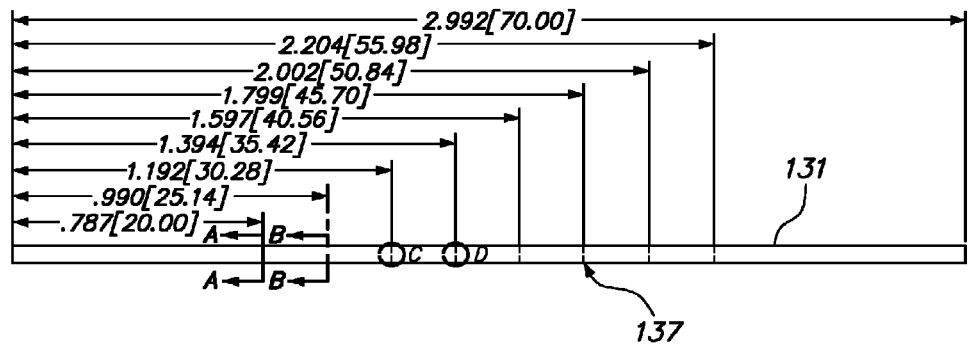
FIG. 20 is a simplified side view of a tubular dispersion member that may be employed in various embodiments of a cryo-ablative balloon instruments used in the system of FIG. 1A.
Figure 20B:
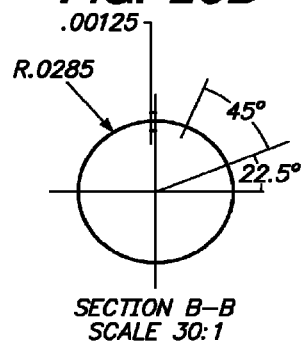
FIGS. 20A-B are sectional views taken along lines A-A and B-B.
Figure 20A:
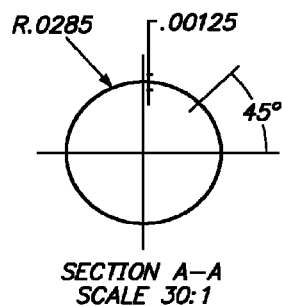
Figure 20C:
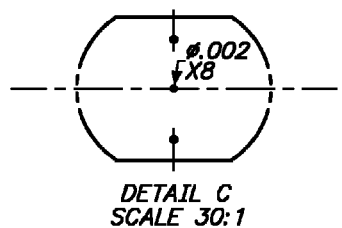
FIGS. 20C-D are exploded views taken along lines C-C, and D-D, respectively, in FIG. 20.
Figure 20D:
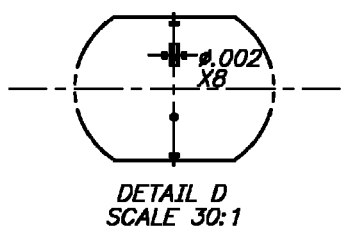

Gas formed as a result of coolant evaporation in the balloon interior (not shown in FIG. 2) is carried back through the exhaust lumen 73 in the elongate body 28, and released through a relief valve (not shown) at a proximal end thereof. In particular, the closed system including the exhaust lumen 73 allows for passage of the (very cold) exhaust gas out of the patient's body, without allowing the gas to directly contact and potentially harm the healthy esophageal, throat and mouth tissue. This is a significant improvement over prior art systems that spray the coolant fluid directly on the esophagus wall. FIG. 20 is a simplified side view of one embodiment of a fluid dispersion tube 131 having a series of axially displaced fluid dispersion apertures 137, which may be employed in various embodiments of cryo-ablative balloon instruments used in the system of FIG. 1A. FIGS. 20A-B are sectional views taken along lines A-A and B-B, and FIGS. 20C-D are exploded views taken along respective lines C-C and D-D, respectively, illustrating the formation and dimensions of the fluid dispersion apertures 137 in the fluid dispersion tube 131 in FIG. 20. Again, a fluid tight seal (not shown) is preferably provided at the distal end of the dispersion tube 131 to force fluid flow through the respective fluid apertures 137.

Figure 5:
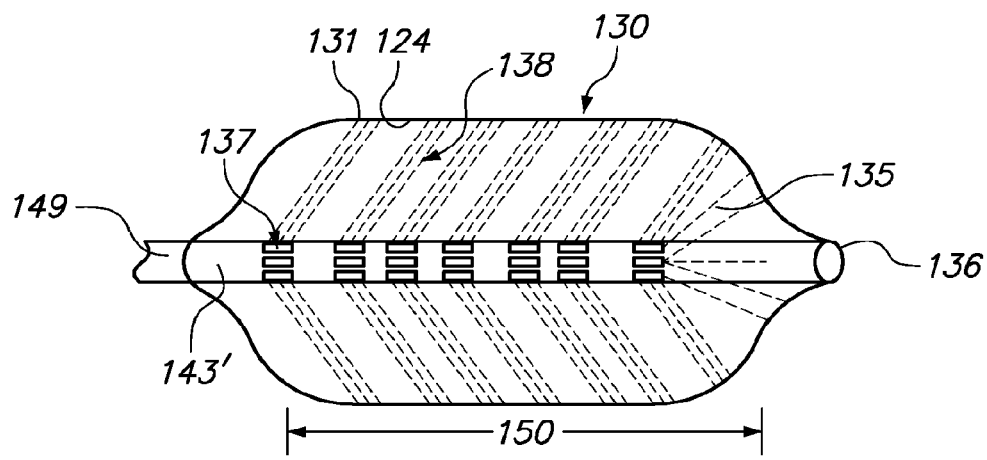
FIG. 5 is a simplified, partially cut-away perspective view of an alternate cryogenic balloon embodiment for use in the system of FIG. 1A, in which the coolant dispersion apertures are formed out of flaps cut into the tubular dispersion member body, with the most distal edge of the flap remaining attached to the dispersion member body, and the proximal end depressed into the interior dispersion member lumen to form a directional ramp for dispersing coolant into the balloon interior.
Figure 5A:
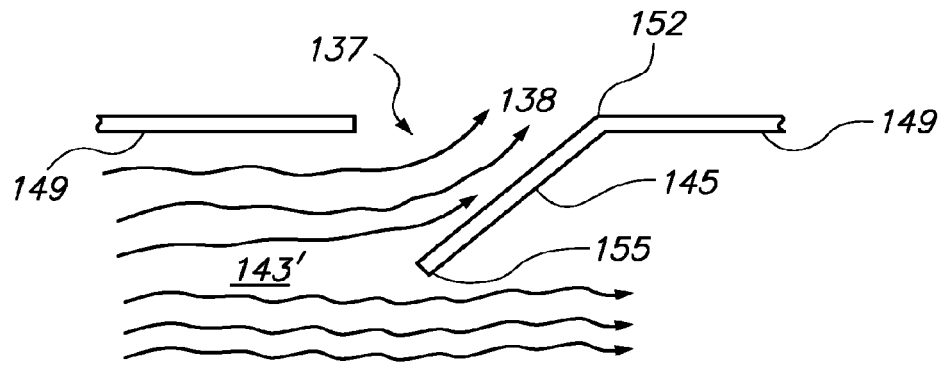
FIG. 5A is a close-in side view of a fluid dispersion aperture ramp in the embodiment of FIG. 5.

A variety of fluid dispersion member designs are envisioned and contemplated for use in embodiments of the disclosed inventions. FIGS. 5 and 5A depict an alternate cryogenic balloon 130 that may be carried distally on the elongate instrument body 28 of the instrument of system 20. As with balloon 30, balloon 130 may be constructed of a compliant or semi-compliant material, and includes a wall 131, with an interior surface 124 of the wall 131 defining an interior 135 of the balloon 130. A dispersion tube 149 is coupled to (or alternatively formed from) a distal end portion of elongate body 28, extending through the balloon interior 135 to a distal balloon end anchor 136. The dispersion tube 149 has a plurality of coolant dispersion apertures 137 in fluid communication with the respective supply lumen 43 and balloon interior 135, wherein the coolant dispersion apertures 137 are sized and located along the dispersion tube 149 such that pressurized coolant 138 in the supply lumen 43 (and dispersion tube lumen 143') will enter the balloon interior 135 in the form of a liquid spray 138 that contacts and provides (due to rapid evaporation of the liquid coolant) substantially uniform cooling of an active treatment length or region 150 of the interior balloon wall surface 124.

More particularly, the axially and circumferentially spaced coolant dispersion apertures 137 in the embodiment of FIG. 5 are formed from rectangular flaps 145 cut into the dispersion tube 149. As best seen in FIG. 5A, the most distal edge 152 of each flap 145 remains attached to the dispersion tube 149, with the proximal flap end 155 depressed into the supply lumen 43 to form a directional ramp for dispersing coolant 138 flowing in the supply lumen into the balloon interior 135. The proximal flap ends 155 may optionally be bonded to an internal mandrel (not shown) positioned within the inner lumen 143' to add stability.

Figure 6:
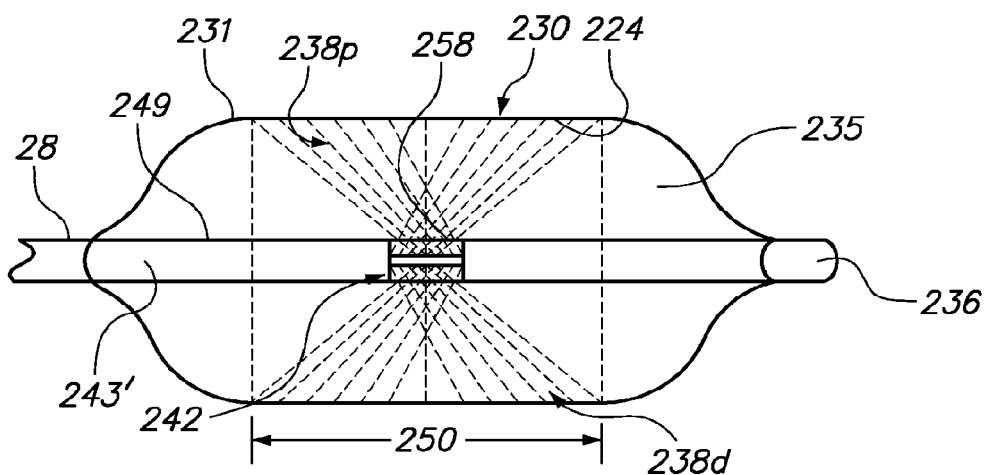
FIG. 6 is a simplified, partially cut-away perspective view of another alternate cryogenic balloon embodiment for use in the system of FIG. 1A, in which a centrally located diffuser and reflector combination are used to direct coolant from the dispersion member lumen against the balloon wall.

FIG. 6 depicts another alternate cryogenic balloon 230 that may be carried distally on the elongate instrument body 28 of system 20. As with balloons 30 and 130, balloon 230 may be constructed of a compliant or semi-compliant material, and includes a wall 231, with an interior surface 224 of the wall 231 defining an interior 235 of the balloon 230. A dispersion tube 249 coupled to (or alternatively is formed from) a distal end portion of elongate body 28, and extends through the balloon interior 235 to a distal balloon end anchor 236. Instead of a plurality of coolant dispersion apertures as employed in the previously described embodiments, one or more diffusers 242 are provided on the dispersion tube 249, each diffuser 242 configured to direct a liquid spray of coolant 238 from the dispersion tube lumen onto the interior balloon wall surface (as indicated by reference number 238d).

Figure 6A:
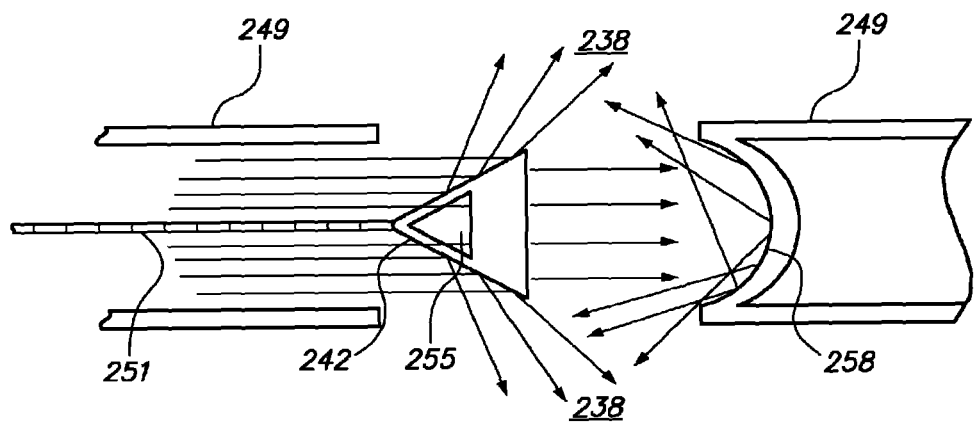
FIG. 6A is a close up of an embodiment of a diffuser/deflector assembly for use in the dispersion member depicted in FIG. 6.

The embodiment of FIG. 6 is also equipped with one or more (optional) deflectors 258 provided on the dispersion tube 249, each deflector 258 located adjacent distally of a respective diffuser 242. The deflector(s) 258 are configured to deflect at least a portion of the fluid coolant spray (as indicated by reference number 238p) originally directed (or allowed to pass by) by a respective diffuser 242, with the collective result of the arrangement of distally directed diffusers 242 and proximally directed deflectors 258 being a substantially uniform spraying of coolant on the interior balloon wall 224 within an active treatment region 250 of the balloon 230. FIG. 6A depicts one embodiment of a respective diffuser/deflector pair 242/258.

The cryogenic balloons (30, 130, 230) disclosed and described herein are preferably made from a flexible, at least semi-compliant polymer, such as polyether block amide (Pebax®) or nylon as is well-known in the art, providing a reasonable and serviceable degree of thermal conductivity in the balloon wall in the active treatment region. However, it may be desirable to incorporate materials having relatively high thermal conductivity in the balloon wall to increase uniformity in balloon wall temperature within the active treatment region of the balloon. On the other hand, such increased thermal conductivity should not come at the expense of loss of adequate compliance or, in some embodiments, balloon wall transparency. Thus, it may be desirable to form a cryogenic balloon for use in the system 20 of FIG. 1 out of a composite material structure, including a first, at least semi-compliant polymer material, and a second material having relatively high thermal transfer properties. Representative high thermal conductivity materials may include carbon nano-tubes, graphite, ultra-thin metal fibers, including silver, gold, stainless steel, nitinol, diamond like carbon coatings, pyrolytic carbon, and boron nitride coatings. The materials may be attached to a surface (interior or exterior) of the balloon wall, e.g., using known vapor deposition, plating or uniform coating processes, or may be embedded or impregnated within the balloon wall.

Figure 7:
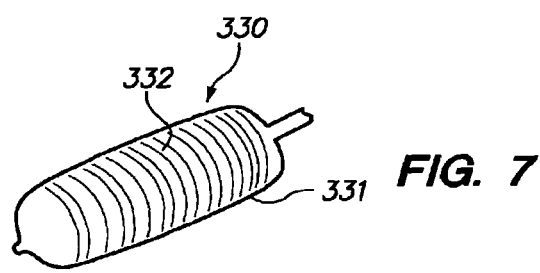
FIGS. 7-8 are perspective views of alternate embodiments of a balloon body that may be used in combination with any of the cryogenic instrument embodiments disclosed herein, in which thin strips or fibers of metallic material having relatively high thermal conductivity are attached to, or embedded in, the balloon wall.
Figure 8:
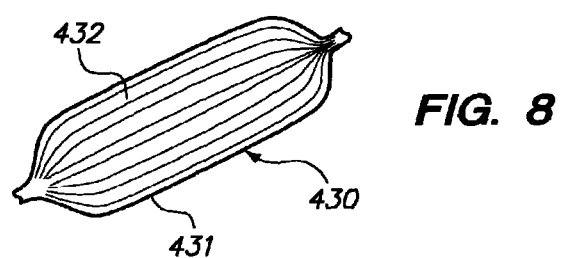

By way of example, FIG. 7 depicts one embodiment of a composite material balloon 330 for use (in combination) with any of the cryogenic balloon embodiments disclosed herein, in which a plurality of axially spaced thin metallic strips or fibers 332 are attached to and/or embedded in a polymer balloon wall 331 to increase the overall thermal conductivity of the balloon 330. The strips or fibers 332 are preferably thin and spaced apart sufficiently such that balloon compliance and/or transparency remain adequate. By way of further example, FIG. 8 depicts another embodiment of a composite material balloon 430 for use (in combination) with any of the cryogenic balloon embodiments disclosed herein, in which a plurality of circumferentially spaced thin metallic strips or fibers 432 are attached to and/or embedded in a polymer balloon wall 431 to increase the overall thermal conductivity of the balloon 430. Again, the metallic strips or fibers 432 are preferably thin and spaced apart sufficiently such that balloon compliance and/or transparency remain adequate.

Figure 9:
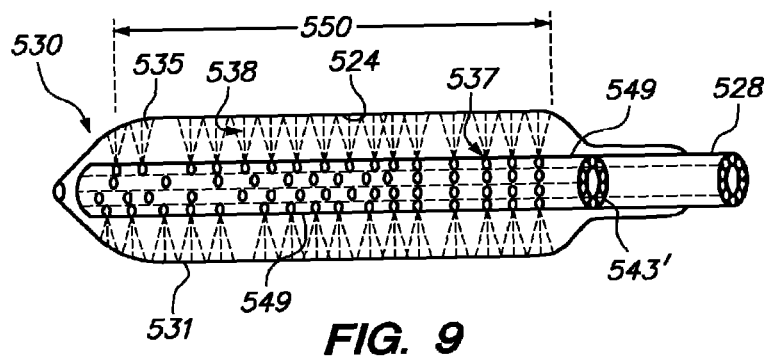
FIGS. 9-10 are simplified, partially cut-away perspective views of still further respective alternate cryogenic balloon embodiments for use in the system of FIG. 1A, in which a plurality of circumferentially spaced coolant supply lumens are provided in the elongate instrument body and dispersion member.

Referring to FIG. 9, in accordance with another embodiment of the disclosed inventions, a cryogenic tissue ablation elongate instrument 528 may be used in a modified version of system 20, and has a proximal supply port (not shown) adapted for coupling with the source of pressurized flowable coolant 39 (e.g., liquid $N_2O$), and a dispersion member 549 coupled to (or alternatively formed out of) a distal end portion of the elongate instrument 528. The elongate body 528 has a plurality of circumferentially spaced coolant supply lumens 543, each in fluid communication with the proximal supply port (not shown), and each extending through the elongate body 528, where they are directly fluidly coupled, or otherwise comprise corresponding respective interior lumens 543' of the dispersion member 549. An expendable balloon 530 is carried on the distal end portion of the elongate body 528, the balloon 530 having a wall 531 with an interior surface 524 defining an interior 535 of the balloon. The dispersion member 549 extends into the balloon interior 535, and has respective pluralities of coolant dispersion apertures 537 formed therein, each plurality of coolant dispersion apertures 537 in fluid communication with a respective one of the coolant supply (and dispersion member) lumens 543 (and 543'). The collective apertures 537 are sized and located on the dispersion member 549 such that a pressurized flowable coolant in the respective supply and dispersion member lumens 543/543' will enter the balloon interior 535 through the respective apertures 537 in the form of a liquid spray 538 that contacts and provides (due to rapid evaporation) substantially uniform cooling of the interior wall surface 524 of a treatment region 550 of the balloon.

Each plurality of coolant dispersion apertures 537 preferably includes a first aperture having a first aperture size in communication with a respective coolant supply lumen 543, and a second aperture located distally on the elongate member 549 from the first aperture in communication with the same respective coolant supply lumen 543, the second aperture having a second aperture size the same or greater than the first aperture size, as needed to account for pressure losses in the respective supply lumen 543, while maintaining substantially uniform output spray 538. In the illustrated embodiment of FIG. 9, the respective dispersion apertures 537 are provided in sets of circumferentially spaced apertures along the dispersion member 549 within the balloon interior 535, each set including respective apertures 537 in fluid communication with a corresponding one of the respective coolant supply lumens 543.

Figure 10:
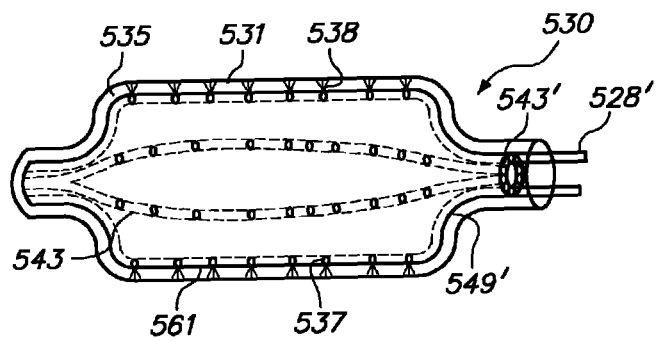

FIG. 10 shows a variation of the embodiment of FIG. 9, in which the portion of the dispersion member (designated 549') extending into the balloon interior (designated 535') is itself an expandable body, with the respective coolant dispersion apertures 537 located on an exterior surface 561 of the "inner" expandable body 549'.

Figure 11B:
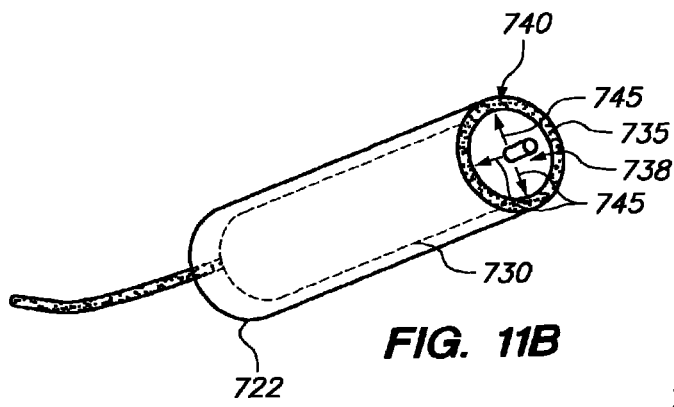
FIGS. 11A-B are distal end perspective views of an embodiment of a cryogenic balloon body shown in a collapsed configuration when initially positioned within an esophagus (FIG. 11A), and in an expanded treatment configuration (FIG. 11B) after having smoothed out the esophageal wall tissue to be treated.
Figure 11A:
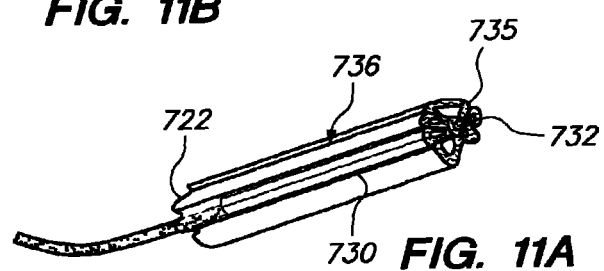

As mentioned previously, the cryogenic balloon embodiments disclosed and described herein are preferably able to be positioned in an esophagus to be treated through a standard working channel of a GI gastroscope. By way of illustration, FIGS. 11A-B depict a perspective view of a cryogenic balloon body 730 that may be employed in combination any of the embodiments described herein for use in system 20. The balloon body 730 is depicted in both a collapsed delivery configuration 732 (FIG. 11A) and an expanded treatment configuration 738 (FIG. 11B). The collapsed delivery configuration 732 is shown positioned within an esophagus 722 in its relaxed state and which is characterized by the esophagus wall 735 being collapsed in the radial direction and gathered into longitudinally oriented folds 736 around the collapsed balloon body 732. Upon expansion of the balloon 730 to its treatment configuration 738, the esophagus wall 735 is expanded and smoothed to configuration 740 (indicated by arrows 745 in FIG. 11B).

The profile of the expanded treatment balloon configuration 738 is preferably slightly greater than the interior of the esophagus 722 such that, when the balloon 730 is transitioned from its collapsed delivery profile 732 to its expanded profile 738, an exterior wall surface of the balloon contacts and smoothes the esophageal wall tissue, providing for more uniform thermal contact with the balloon wall, and as a consequence, more uniform cooling of the esophageal tissue, resulting in a more uniform depth of tissue ablation from the treatment. At the same time, the cryogenic balloon 730 preferably has a compliance such that, as it transitions from its collapsed delivery profile 732 to its expanded treatment profile 738, the force of the esophageal wall tissue exerted back on the balloon wall causes the balloon 730 to assume a more elongated shape than it has in the absence of such force. The exterior wall surface of the balloon 730 is preferably made of or coated with a lubricious material to facilitate its positioning and smoothing of the esophageal wall tissue. Built-in tensioning elements (not shown) may optionally be added to reduce the profile of the balloon 30, and ease in its withdrawal back through the working channel of the gastroscope after treatment of the esophagus 722 is completed.

Figure 14:
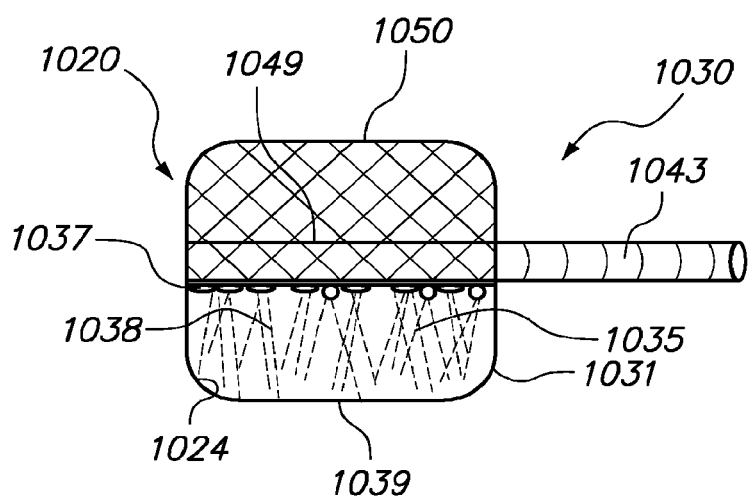
FIG. 14-17 are simplified, partially cut-away perspective views of still further cryogenic balloon embodiments for use in the system of FIG. 1A.

In some circumstances, it may be advantageous for ablating a more localized area of the esophageal tissue wall. Instruments designed more specifically for this purpose are shown in FIGS. 14-16. These instruments have an identical or substantially similar proximal portion as instrument 21 in system 20, i.e., controller 34 operatively coupled with a canister of pressurized coolant 39), and are similarly operated and controlled. Referring to FIG. 14, one such cryogenic tissue ablation instrument 1020 includes an elongate flexible body having a proximal supply port (not shown) adapted for coupling with a source of a pressurized flowable coolant, and a coolant supply lumen 1043 in fluid communication with the proximal supply port and extending through the elongate body to a distal end portion thereof. An expandable balloon 1030 is carried on the distal end of the elongate body, the balloon 1030 having a (preferably at least semi-compliant) wall 1031, wherein an interior surface 1024 of the wall 1031 defines an interior 1035 of the balloon 1030.

A dispersion member 1049 coupled to or otherwise formed from a distal end portion of the elongate body extends within the balloon interior 1035 and has a plurality of coolant dispersion apertures in fluid communication with the supply lumen 1043, the dispersion apertures being sized and positioned in the dispersion member 1049 with respect to the balloon wall 1031, such that a pressurized flowable coolant in the supply lumen 1043 will enter the balloon interior 1035 through the apertures 1037 in the form of a liquid spray 1038 that contacts and provides (due to rapid evaporation) substantially uniform cooling of an energy delivery portion 1039 of the balloon wall 1031. Notably, the energy delivery portion of the balloon wall 1039 is side facing, with the coolant dispersion apertures 1037 positioned relative to the balloon wall portion 1039 so that the coolant spray 1038 is directed radially relative to the longitudinal axis of the elongate instrument body. In order to avoid unwanted collateral tissue cooling, those portions of the balloon wall 1031 that are not part of the energy delivery portion 1039 are coated with an insulation layer 1050.

Figure 15A:
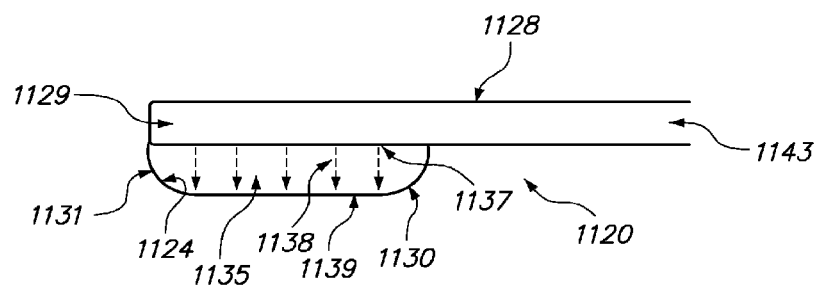
Figure 15B:
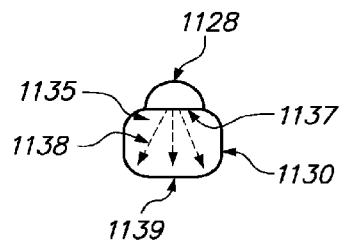
Figure 16:
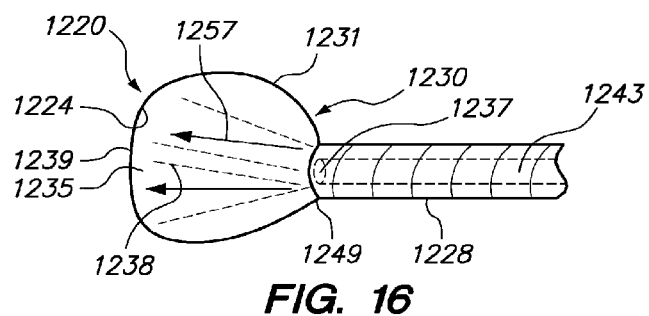

FIGS. 15A-B depict an alternate embodiment of a "side firing" cryogenic balloon instrument 1120, which includes an elongate flexible body 1128 having a proximal supply port (not shown) adapted for coupling with a source of a pressurized flowable coolant, a distal end portion 1129 sized for introduction into a human esophagus, and a coolant supply lumen 1143 in fluid communication with the proximal supply port and extending through the elongate body 1128 to the distal end portion 1129. An expandable balloon 1130 is carried on the distal end portion 1129 of the elongate body 1128, the balloon 1130 having a (preferably at least semi-compliant) wall 1131, wherein an interior surface 1124 of the wall 1131 defines an interior 1135 of the balloon 1130.

The distal end portion 1129 of the elongate body 1128 is attached to the balloon wall 1131 (rather than extending through the balloon interior as in previous embodiments), and has a plurality of coolant dispersion apertures 1137 in fluid communication with the respective supply lumen 1143 and balloon interior 1135. The dispersion apertures are sized and positioned on the elongate body 1129 with respect to the balloon wall 1131, such that a pressurized flowable coolant in the supply lumen 1143 will enter the balloon interior 1135 through the apertures 1137 in the form of a liquid spray 1138 that contacts and provides (due to rapid evaporation) substantially uniform cooling of an energy delivery portion 1139 of the balloon wall 1131. As with instrument 1020, the energy delivery portion 1139 of the balloon wall 1131 of instrument 1120 is side facing, with the coolant dispersion apertures 1137 positioned relative to the energy delivery balloon wall portion 1139 so that the coolant spray 1138 is directed radially relative to the longitudinal axis of the elongate instrument body 1128.

FIG. 16 depicts a further embodiment of a more localized cryogenic balloon instrument 1220, which includes an elongate flexible body 1228 having a proximal supply port (not shown) adapted for coupling with a source of a pressurized flowable coolant, a distal end portion sized for introduction into a human esophagus, and a coolant supply lumen 1243 in fluid communication with the proximal supply port and extending through the elongate body 1228 to the distal end portion thereof. An expandable balloon 1230 is coupled to the distal end portion of the elongate body 1228, the balloon 1230 having a (preferably at least semi-compliant) wall 1231, wherein an interior surface 1224 of the wall 1231 defines an interior 1235 of the balloon 1230. One or more distal facing coolant dispersion apertures 1237 in fluid communication with the respective supply lumen 1243 and balloon interior 1235 are located at the juncture between the distal end portion of the elongate body 1228 and the balloon wall 1231. The one or more dispersion apertures are sized and positioned with respect to the balloon wall 1231, such that a pressurized flowable coolant in the supply lumen 1243 will enter the balloon interior 1235 through the aperture(s) 1237 in the form of an axially directed liquid spray 1238 that contacts and provides (due to rapid evaporation) substantially uniform cooling of a distal facing energy delivery portion 1239 of the balloon wall 1231.

Figure 17:
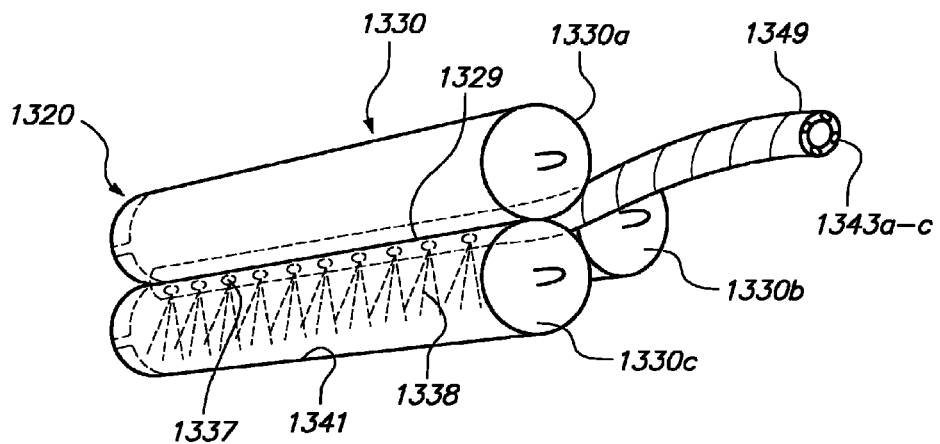

Referring to FIG. 17, a further alternative cryogenic tissue ablation instrument 1320 for use with the system 20 of FIG. 1 includes an elongate flexible body having a distal portion 1329 sized for introduction into a human esophagus, and a plurality of supply lumens 1343 in fluid communication with one or more respective proximal coolant supply ports (not shown) and extending through the elongate body to the distal portion 1329; and an expandable multi-lobe balloon 1330 carried on the distal portion 1329 and having a plurality of isolated balloon chambers 1330A-C. The distal portion 1329 extends through a central region of (i.e., between the lobes of) the balloon 1330, each of the coolant supply lumens 1343 may be in fluid communication with a respective one of the interior balloon chambers 1330A-C via a respective plurality of coolant dispersion apertures 1337 in the distal portion 1329, wherein the respective dispersion apertures 1337 are sized and positioned on the elongate body distal portion 1329 such that a pressurized flowable coolant in one of the supply lumens 1343 will enter the respective interior balloon chamber (chamber 1330C is shown in FIG. 17 by way of illustration) through the respective dispersion apertures 1337 in the form of a liquid spray 1338 that contacts and cools of an interior wall surface 1341 of the respective chamber (1330C). Additionally or alternatively, the isolated balloon chambers 1330A-C may be in fluid communication with independent fluid or gas inflation sources through respective lumens extending through the elongate body (not shown).

A system including the multi-lobe balloon instrument 1320 further includes a source of pressurized flowable coolant fluidly coupled to the respective one or more coolant supply ports of the instrument, and a controller operatively coupled with the source of pressurized flowable coolant so as to controllable release the coolant into a respective one or more of the supply lumens 1343.

Prototype Fabrication and Testing

Figure 19:
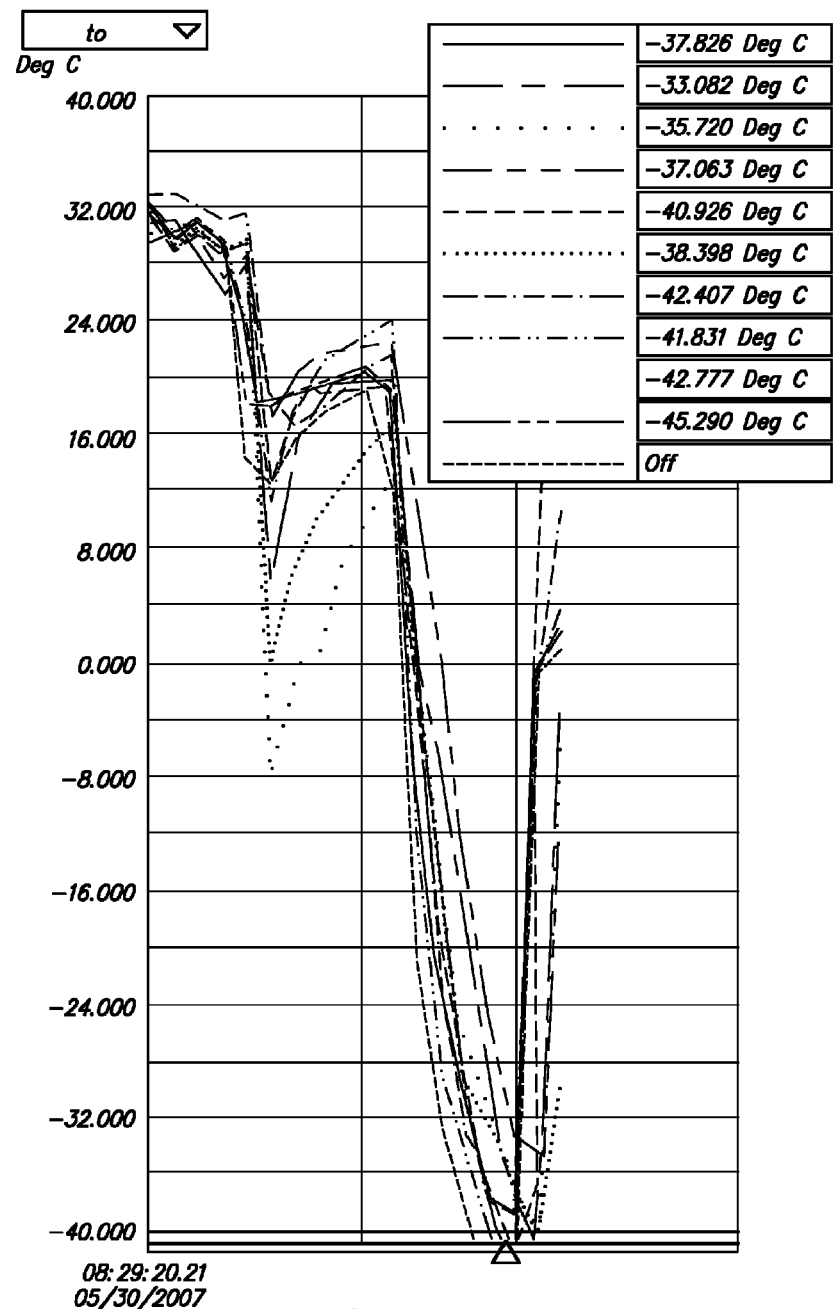
FIG. 19 is a time-versus-temperature plot of temperatures measured using thermocouples positioned to monitor temperature at multiple axial and circumferential locations on the outer surface of a prototype cryogenic balloon constructed in accordance with one embodiment of the disclosed inventions, demonstrating that temperatures along a 4 cm length of the balloon were substantially uniform during cooling of the balloon wall.

Large diameter cryogenic balloon ablation instruments were fabricated to evaluate temperature profiles at the balloon surface and in open cell foam models immersed in 37° C. water external to the balloon. The instruments were fabricated from endoscopic controlled radial step expansion (CRE) dilation balloons having diameters that range from 18 to 20 mm, depending on the inflation pressure. The balloons were attached to enlarged, 0.017 inch (ID) instrument shafts similar to those used for the PolarCath™ vascular cryogenic balloon catheter distributed by Boston Scientific Corporation. Standard PolarCath™ nitrous oxide $N_2O$ cylinders and control units were used for inflation of the prototypes. The control units were reprogrammed to run the desired test cycles. Bench top tests in body temperature water showed that balloon surface temperatures of −40° C. were reached within 15 seconds, as illustrated in the time-versus-temperature plot in FIG. 19, where each x-axis mark represents 10 seconds. Temperatures were measured along the length of the balloons and shown to be uniform over approximately 4 cm. The dispersion tube apertures were 0.002 inches in diameter and positioned in eight longitudinally spaced rings. In particular, each ring included eight apertures formed by laser drilling uniformly spaced around the circumference of the diffusion tube, offset from adjacent ring apertures by 22.5°. Diffuser tube details are shown in FIGS. 20A-D. The 0.057 inch diameter polyimide diffuser tube was fabricated separately and adhesively bonded to the fluid supply lumen and instrument shaft.

It will be appreciated that various embodiments of the disclosed inventions may be used to perform methods of treating esophageal tissue using a cryogenic balloon. Such methods of use are in themselves further embodiments of the disclosed inventions. By way of example, in one such embodiment, a method is provided for ablating esophageal wall tissue using a cryogenic balloon instrument, the instrument comprising an elongate flexible member carrying an expandable balloon on a distal end thereof; the balloon having a collapsed delivery shape and an expanded treatment shape. In accordance with this embodiment, the method includes (i) delivering the cryogenic balloon in its delivery shape through a working channel of an endoscopic instrument to a location in an esophagus to be treated; (ii) expanding the cryogenic balloon so that an outer surface of the balloon contacts and smoothes esophageal wall tissue to be treated; and (iii) delivering a pressurized flowable coolant from a source external to the patient through a supply lumen in the elongate body and out one or more coolant dispersion apertures in the elongate body in fluid communication with the balloon interior, the one or more coolant dispersion apertures being sized and positioned relative to an interior wall of the balloon such that the pressurized flowable coolant enters the balloon interior in the form of a liquid spray that contacts and provides substantially uniform cooling of the interior balloon wall surface of a treatment region of the balloon. The gas formed as a result of coolant evaporation is carried through a channel in the elongated flexible instrument and released through a relief valve at a proximal end of the instrument.

While certain exemplary embodiments have been described herein and shown in the accompanying drawings, it is to be understood that such embodiments are merely illustrative and not restrictive of the inventive concepts and features, and that the inventions disclosed herein are not limited to the specific constructions and arrangements shown and described, as various further and other modifications may occur to those skilled in the art upon studying this disclosure.

What is claimed is:

1. A cryogenic tissue ablation instrument, comprising:
an elongate flexible body having a proximal supply port adapted for coupling with a source of a pressurized flowable coolant and a supply lumen in fluid communication with the proximal supply port and extending through the elongate body to a distal portion thereof;
a dispersion member coupled to or formed out of the distal portion of the elongate body, the dispersion member including an interior lumen in fluid communication with or otherwise comprising a portion of the supply lumen, wherein a first circumferential portion of the dispersion member relative to a longitudinal axis of the elongate flexible body does not include apertures, and a second circumferential portion of the dispersion member relative to the longitudinal axis of the elongate flexible body includes one or more side-facing coolant dispersion apertures; and
an expandable balloon carried on the distal portion of the elongate body, the balloon having a wall comprising a circumferential energy delivery portion relative to the longitudinal axis of the elongate flexible body and a circumferential non-energy delivery portion relative to the longitudinal axis of the elongate flexible body, wherein the energy delivery portion and the non-energy delivery portion of the balloon, except at distal and proximal ends of the balloon, do not contact the elongate flexible body along the longitudinal axis when the balloon is expanded, an interior surface of the wall defining an interior of the balloon, the dispersion member in fluid communication with the respective supply lumen and balloon interior, wherein the first portion of the dispersion member only faces the non-energy delivery portion of the balloon wall, and the second portion of the dispersion member only faces the energy delivery portion of the balloon wall such that the pressurized flowable coolant in the supply lumen enters the balloon interior through the one or more side-facing coolant dispersion apertures in the form of a spray that provides substantially uniform cooling of the energy delivery portion of the balloon wall and that provides substantially less cooling of the non-energy delivering portion of the balloon wall.

2. The cryogenic tissue ablation instrument of claim 1, wherein an exterior surface of the balloon wall comprises or is coated with a lubricious material.

3. The cryogenic tissue ablation instrument of claim 1, further comprising one or more temperature sensors carried on or in the dispersion member.

4. The cryogenic tissue ablation instrument of claim 1, further comprising one or more temperature sensors carried on or in the energy delivery portion of the balloon wall.

5. The cryogenic tissue ablation instrument of claim 1, wherein the balloon wall comprises an optically clear material.

6. The cryogenic tissue ablation instrument of claim 1, wherein the balloon comprises a semi-compliant material.

7. The cryogenic tissue ablation instrument of claim 1, wherein a shape of the one or more side-facing coolant dispersion apertures is selected from the group consisting of circular, rectangular or elliptical shapes.

8. A cryogenic tissue ablation instrument, comprising:
an elongate flexible body having a proximal supply port adapted for coupling with a source of a pressurized flowable coolant and a supply lumen in fluid communication with the proximal supply port and extending through the elongate body to a distal portion thereof;
a dispersion member coupled to or formed out of the distal portion of the elongate body, the dispersion member including an interior lumen in fluid communication with or otherwise comprising a portion of the supply lumen, wherein a first circumferential portion of the dispersion member relative to a longitudinal axis of the elongate flexible body does not include apertures, and a second circumferential portion of the dispersion member relative to the longitudinal axis of the elongate flexible body includes one or more side-facing coolant dispersion apertures; and
an expandable balloon carried on the distal portion of the elongate body, the balloon having a wall comprising a circumferential energy delivery portion relative to the longitudinal axis of the elongate flexible body, and a circumferential insulated portion relative to the longitudinal axis of the elongate flexible body, wherein the energy delivery portion and the insulated portion of the balloon, except at distal and proximal ends of the balloon, do not contact the elongate flexible body along the longitudinal axis when the balloon is expanded, an interior surface of the wall defining an interior of the balloon, the dispersion member in fluid communication with the respective supply lumen and balloon interior, wherein the first portion of the dispersion member only faces the insulated portion of the balloon wall, and the second portion of the dispersion member only faces the energy delivery portion of the balloon wall such that the pressurized flowable coolant in the supply lumen enters the balloon interior through the one or more side-facing coolant dispersion apertures in the form of a spray that provides substantially uniform cooling of the energy delivery portion of the balloon wall and that provides substantially less cooling of the insulated portion of the balloon wall.

9. The cryogenic tissue ablation instrument of claim 8, wherein an exterior surface of the balloon wall comprises or is coated with a lubricious material.

10. The cryogenic tissue ablation instrument of claim 8, further comprising one or more temperature sensors carried on or in the dispersion member.

11. The cryogenic tissue ablation instrument of claim 8, further comprising one or more temperature sensors carried on or in the energy delivery portion of the balloon wall.

12. The cryogenic tissue ablation instrument of claim 8, wherein the balloon wall comprises an optically clear material.

13. The cryogenic tissue ablation instrument of claim 8, wherein the balloon comprises a semi-compliant material.

14. The cryogenic tissue ablation instrument of claim 8, wherein a shape of the one or more side-facing coolant dispersion apertures is selected from the group consisting of circular, rectangular or elliptical shapes.

15. A cryogenic tissue ablation instrument, comprising:
an elongate flexible body having a proximal supply port adapted for coupling with a source of a pressurized flowable coolant and a supply lumen in fluid communication with the proximal supply port and extending through the elongate body to a distal portion thereof;
a dispersion member coupled to or formed out of the distal portion of the elongate body, the dispersion member including an interior lumen in fluid communication with or otherwise comprising a portion of the supply lumen, wherein a first circumferential portion of the dispersion member relative to a longitudinal axis of the elongate flexible body does not include apertures, and a second circumferential portion of the dispersion member relative to the longitudinal axis of the elongate flexible body includes one or more side-facing coolant dispersion apertures; and
an expandable balloon carried on the distal portion of the elongate body, the balloon having a wall comprising a circumferential energy delivery portion relative to the longitudinal axis of the elongate flexible body and a circumferential non-energy delivery portion relative to the longitudinal axis of the elongate flexible body, wherein a distance of the wall of the energy delivery portion from the longitudinal axis of the elongate flexible body is substantially equal to a distance of the wall of the non-energy delivery portion from the longitudinal axis of the elongate flexible body when the balloon is expanded, an interior surface of the wall defining an interior of the balloon, the dispersion member in fluid communication with the respective supply lumen and balloon interior, wherein the first portion of the dispersion member only faces the non-energy delivery portion of the balloon wall, and the second portion of the dispersion member only faces the energy delivery portion of the balloon wall such that the pressurized flowable coolant in the supply lumen enters the balloon interior through the one or more side-facing coolant dispersion apertures in the form of a spray that provides substantially uniform cooling of the energy delivery portion of the balloon wall and that provides substantially less cooling of the non-energy delivering portion of the balloon wall.

16. The cryogenic tissue ablation instrument of claim 15, wherein an exterior surface of the balloon wall comprises or is coated with a lubricious material.

17. The cryogenic tissue ablation instrument of claim 15, further comprising one or more temperature sensors carried on or in the dispersion member.

18. The cryogenic tissue ablation instrument of claim 15, further comprising one or more temperature sensors carried on or in the energy delivery portion of the balloon wall.

19. The cryogenic tissue ablation instrument of claim 15, wherein the balloon wall comprises an optically clear material.

20. The cryogenic tissue ablation instrument of claim 15, wherein the balloon comprises a semi-compliant material.

21. The cryogenic tissue ablation instrument of claim 15, wherein a shape of the one or more side-facing coolant dispersion apertures is selected from the group consisting of circular, rectangular or elliptical shapes.

* * * * *